(12) United States Patent
Toida

(10) Patent No.: US 6,999,608 B2
(45) Date of Patent: Feb. 14, 2006

(54) IMAGING APPARATUS

(75) Inventor: Masahiro Toida, Kaisei-machi (JP)

(73) Assignee: Fuji Photo Film Co., Ltd., Kanagawa-ken (JP)

(*) Notice: Subject to any disclaimer, the term of this patent is extended or adjusted under 35 U.S.C. 154(b) by 673 days.

(21) Appl. No.: 09/984,854

(22) Filed: Oct. 31, 2001

(65) Prior Publication Data

US 2002/0051512 A1 May 2, 2002

(30) Foreign Application Priority Data

Oct. 31, 2000 (JP) .......................... 2000-332361
Oct. 12, 2001 (JP) .......................... 2001-315464

(51) Int. Cl.
*G06K 9/00* (2006.01)

(52) U.S. Cl. .................. 382/131; 382/274; 382/321; 356/479

(58) Field of Classification Search ................ 382/131, 382/128, 274, 321; 600/479; 356/479, 39; 378/24; 377/10; 128/922
See application file for complete search history.

(56) References Cited

U.S. PATENT DOCUMENTS

| | | | | |
|---|---|---|---|---|
| 5,317,148 A | * | 5/1994 | Gray et al. | 250/227.26 |
| 5,321,501 A | * | 6/1994 | Swanson et al. | 356/479 |
| 5,383,467 A | * | 1/1995 | Auer et al. | 600/342 |
| 5,496,999 A | | 3/1996 | Linker et al. | |
| 5,570,182 A | * | 10/1996 | Nathel et al. | 356/511 |
| 5,582,171 A | * | 12/1996 | Chornenky et al. | 600/425 |
| 6,608,684 B1 | * | 8/2003 | Gelikonov et al. | 356/479 |
| 6,680,780 B1 | * | 1/2004 | Fee | 356/498 |
| 2002/0168161 A1 | * | 11/2002 | Price et al. | 385/123 |

FOREIGN PATENT DOCUMENTS

| | | |
|---|---|---|
| JP | 09-149878 | 6/1997 |
| JP | 2000-097846 | 4/2000 |
| JP | 2000-126188 | 5/2000 |
| WO | WO 92/19930 A1 | 11/1992 |
| WO | WO 98/38907 A1 | 9/1998 |
| WO | WO 99/57507 A1 | 11/1999 |
| WO | WO 00/32102 A1 | 6/2000 |

* cited by examiner

Primary Examiner—Bhavesh M. Mehta
Assistant Examiner—Barry Choobin
(74) Attorney, Agent, or Firm—Sughrue Mion, PLLC

(57) ABSTRACT

An compact imaging apparatus having an OCT function is provided. An image formed of the illuminating-light reflected from a examination area is displayed on a monitor. A signal-light for obtaining an optical tomographic image is guided in a fiber through an insertion portion and projected onto a living tissue measurement area by an illuminating lens. The measurement area is scanned with the signal-light by a Piezo actuator moving the output face of the fiber. An OCT obtaining-portion obtains and displays on a monitor an optical tomographic image by using the interference caused by the signal-light reflected from the measurement area and a reference-light. By performing the scanning with the signal-light using an image-obtaining lens, the need to insert a probe for obtaining an optical tomographic image through a forceps port is eliminated. Therefore, the number of required forceps ports is reduced, and the insertion portion can be made thin.

11 Claims, 2 Drawing Sheets

F I G . 1
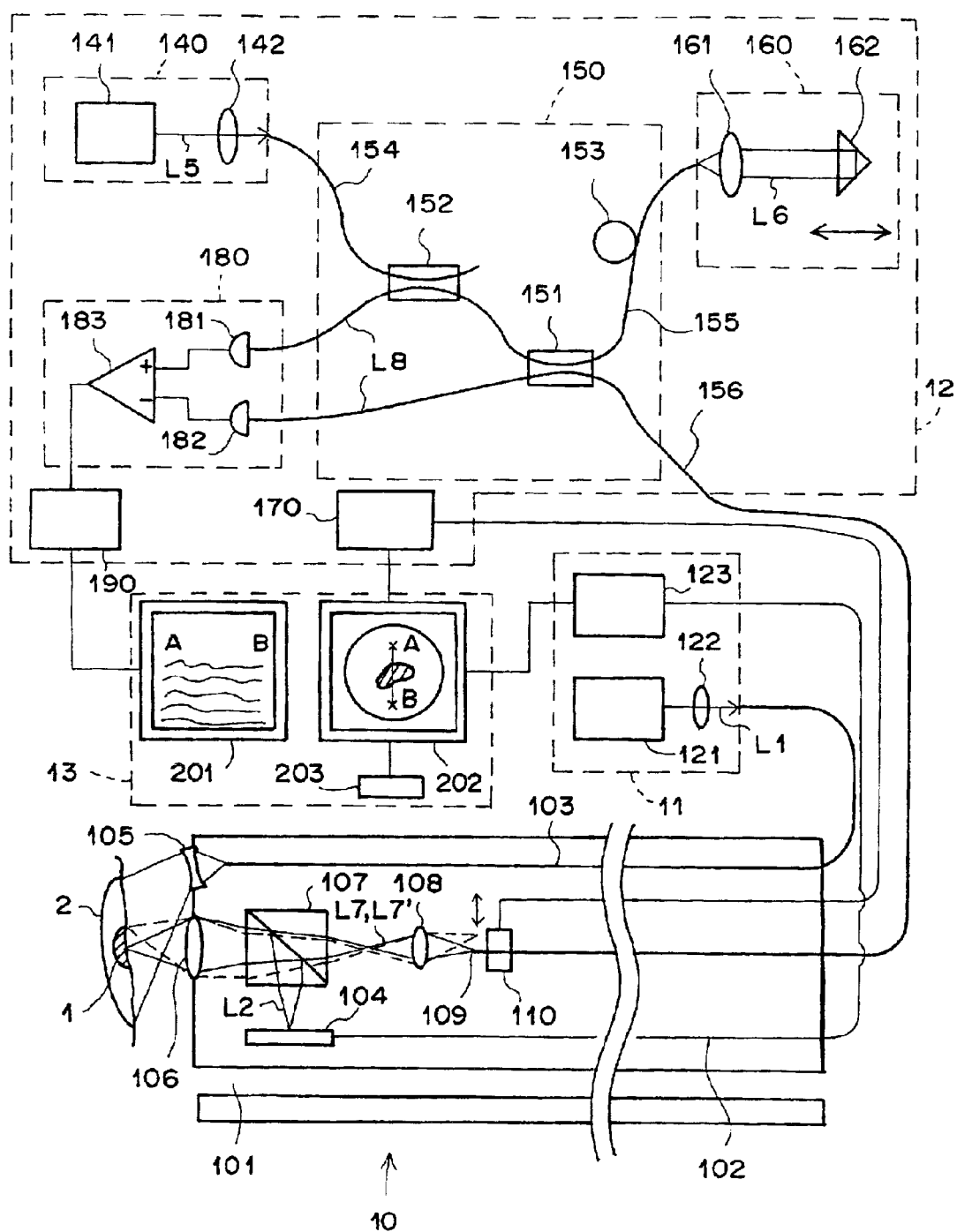

F I G . 2
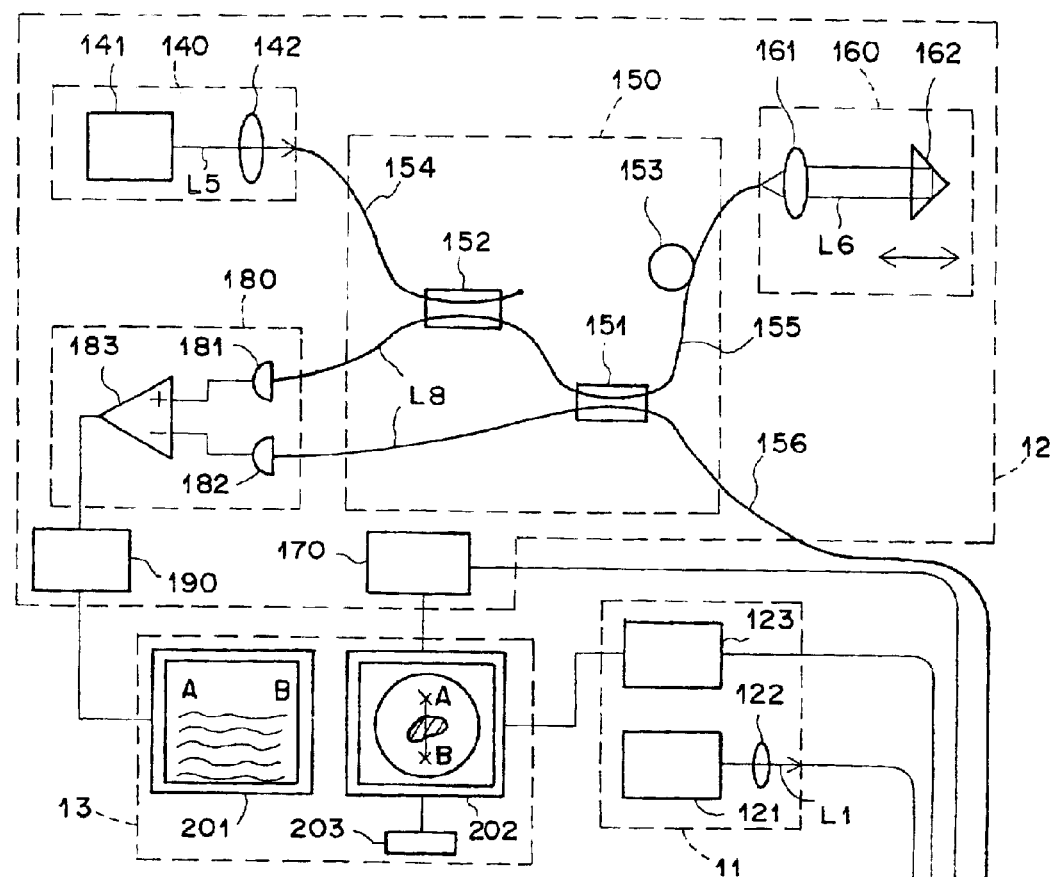
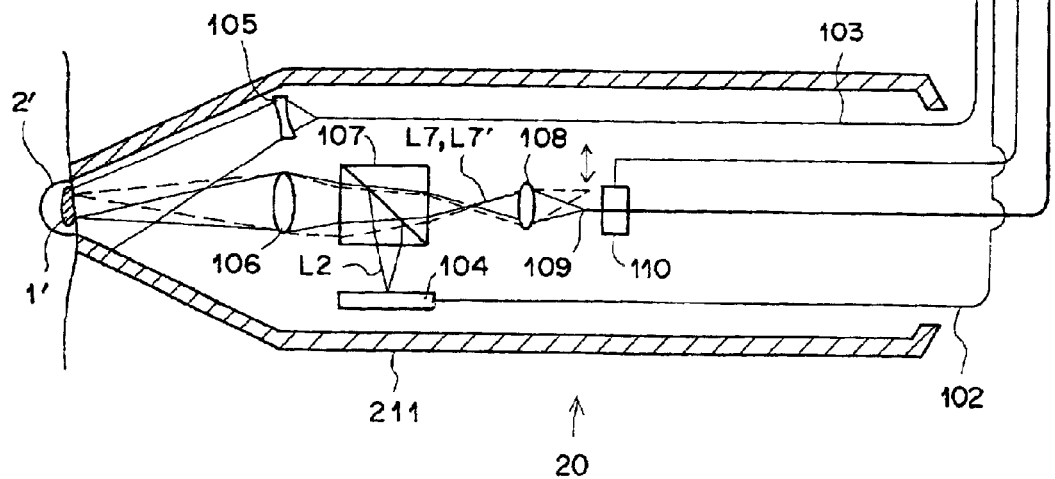

IMAGING APPARATUS

BACKGROUND OF THE INVENTION

1. Field of the Invention

The present invention relates in general to an imaging apparatus, and in particular to an imaging apparatus provided with an OCT function for scanning an examination area of a subject tissue with a signal light, which is a low coherence light, and obtaining an optical tomographic image thereof.

2. Description of the Related Art

There are in use in a variety of medical fields imaging apparatuses that image for observation tissue surfaces of living subjects. If an image obtained by an imaging apparatus is displayed on a monitor or the like, a plurality of people may observe the examination area image. Also, by recording an examination area image, progressive observation and the like will become possible. As these imaging apparatuses, those which utilize electron endoscopes are in wide use. Apparatuses that utilize a pen-form surface examination probe are also known. A conventional electron endoscope is equipped with an imaging element at the distal end of an insertion portion thereof, to be inserted within a body cavity of a patient. It is also often the case that, in a surface examination probe, an imaging element is provided at a distal end of a pen-form probe.

On the other hand, in conventional OCT (Optical Coherence Tomography) apparatuses, in which a low-coherence light is utilized, particularly, OCT apparatuses that obtain an optical tomographic image by measuring the intensity of the interference-light caused by the low-coherence light by heterodyne wave detection are being utilized for obtaining optical tomographic images of the microscopic structure under the fundus of the retina. A detailed description of the aforementioned heterodyne detection OCT apparatus can be found in an article in "O Plus E" Vol. 21, No. 7, pp. 802–804, by Masamitsu Haruna.

According to the aforementioned OCT apparatus: the low-coherence light emitted from a light source formed of an SLD (Super Luminescent Diode) or the like, is separated into a signal-light and a reference-light; the frequency of the signal-light or the reference-light is slightly shifted by use of a Piezo element or the like; the target subject tissue is irradiated with the signal-light and interference is caused between the reflected-light reflected from said target subject tissue at a predetermined depth and the reference-light; the signal strength of the interference signal produced due to said interference is measured by a heterodyne wave detection; and the tomographic data is obtained; wherein, by very slightly moving a movable mirror, etc. disposed above the optical path of the reference-light, causing the length of the optical path of the reference-light to change slightly, the data for a depth of the target subject tissue at which the length of the optical path of the reference-light and the length of the optical path of the signal-light are made to be equal can be obtained.

By utilizing such OCT apparatuses, because the early diagnosis of the depth of penetration of cancer and the like also becomes possible, there is a large demand to obtain an optical tomographic image along with a standard examination area image.

However, in order to employ an imaging apparatus equipped with a surface examination probe and an OCT apparatus, it is necessary to place both said surface examination probe and an OCT detection element in the vicinity of an examination area, thereby requiring a large amount of space in the vicinity of said examination area.

Further, methods of obtaining an optical tomographic image of the interior of a body cavity by utilizing an OCT detection element insertable into the forceps port of an electron endoscope and guiding the signal light as well as the reflected light of the signal light in order employ an imaging apparatus equipped with an endoscope and an OCT apparatus are currently being developed. However, in order to obtain an optical tomographic image by utilizing an OCT detection element inserted into the forceps port of an endoscope, a forceps port must be provided on the endoscope. A problem arises that the insertion portion of an endoscope cannot be made thin. In addition, if implements for performing biopsies or other procedures are to be utilized simultaneously with an OCT detection element, two forceps ports must be provided, further increasing the difficulty in making the insertion portion thin.

SUMMARY OF THE INVENTION

The present invention has been developed in consideration of the circumstances described above, and it is a primary object of the present invention to provide an imaging apparatus that has an OCT function for obtaining an optical tomographic image, while having a compact structure.

The endoscope imaging apparatus according the present invention comprises: an examination area image obtaining means having an illuminating-light emitting means for projecting an illuminating-light onto the examination area, an image obtaining means for obtaining an image formed of the reflected-light reflected from the examination area upon the irradiation thereof with the illuminating-light emitted from the illuminating-light emitting means and which has passed through an image obtaining lens, an examination area image display means for displaying an examination area image based on the image obtained by said image obtaining means; and an OCT means for scanning the examination area with a signal-light, which is a low-coherence light, and obtaining an optical tomographic image of the scanned area using the interference casued between the reflected-light reflected from a predetermined depth of said scanned area upon the scanning thereof with the signal-light, and and a reference-light which has a slight frequency difference with respect to the examination area by passing the signal-light through the inage obtaning lens.

Here, the referent of the term "illuminating-light" is not limited to white-light or other visible light, but also includes types of non-visible light such as infrared light and the like. Further, the referent of the expression "an examination area image based on the image obtained by said image obtaining means" can be an examination area image formed by subjecting the image obtained by the image obtaining means to reflectance-image image processing, or an examination area image formed by subjecting the image obtained by the image obtaining means to any of a number of specialized image-processing processes; etc. As to the specialized image processing processes, for cases in which the illuminating-light is a non-visible light such as infrared light, etc., an image processing process for converting the image obtained by the image obtaining means to an examination area image formed of visible light can be used, etc.

Further, the imaging apparatus according to the present invention further comprises an optical tomographic image display means for displaying an optical tomographic image obtained by the OCT means, which can also be a means for concurrently displaying the examination area image and the optical tomographic image.

Still further, the imaging apparatus according to the present invention may further comprise a position specifying means for arbitrarily specifying two desired points on an examination area image displayed on the examination area image display means, and the OCT means may further comprise a scanning control portion for scanning with the signal-light the scanning area corresponding to the position between the two points specified by use of the position specifying means.

Here, as to the position specifying means, any means that can arbitrarily specify two desired points can be employed. For example, a pen-type interface for specifying two desired points by touching the screen therewith; a means for entering the coordinates of two desired points; a mouse that operates as a cursor for inputting 2 desired points, or the like can be employed thereas.

The OCT means comprises: a light-guiding means for guiding the signal-light; an image forming lens for focusing the signal-light emitted from said light-guiding means onto a position that is conjugate with the image forming surface of the image obtaining means; and a scanning means for moving the output face of the light-guiding means along a flat surface that is substantially parallel to the image forming lens, wherein the image obtaining means, the light-guiding means, the image forming lens, and the scanning means are provided within the endoscope insertion portion, and the scanning control means controls, by use of the scanning means, the positioning of the output face of the light guiding means.

Further, if the examination area is of a living-tissue subject, it is preferable that the low-coherence light is of a wavelength within the 600–1700 nm wavelength range.

Note that according to the present invention, the light source for emitting the low-coherence light is not limited to any specific light source; any light source that emits a low-coherence light can be employed thereas.

According to the imaging apparatus of the present invention: an examination area image formed of the reflected-light reflected from a target subject upon the irradiation thereof by the illuminating-light is passed through the image obtaining lens for obtaining an examination area image; the OCT means carries out scanning with the signal-light; and because it is not necessary to equip the endoscope with separate lenses for obtaining an examination area image and an optical tomographic image, an imaging apparatus can be realized which is provided with an OCT function for obtaining an optical tomographic image while having a compact structure.

If the examination area image and the optical tomographic image are displayed concurrently on the optical tomographic image display means for displaying an optical tomographic image, with the OCT means is provided, an operator can observe both the examination area image and the optical tomographic image concurrently, whereby the overall convenience attained in the practical application of the endoscope apparatus is improved.

In addition, if the endoscope apparatus according to the present invention is provided with a position specifying means for arbitrarily specifying 2 desired points on an examination area image displayed on the examination area image display means, and the OCT means is provided with a scanning control portion for scanning with the signal-light the scanning area corresponding to the position between the two points on the examination area specified by use of the position specifying means, because by simply specifying, by use of the position specifying means, 2 desired points on the examination area image, an operator can obtain an optical tomographic image of the scanning area corresponding to the examination area between said 2 specified desired points, it becomes unnecessary to perform a troublesome manual operation for causing the signal-light to guided to a desired position, and an optical tomographic image of a desired position can be accurately obtained.

If the OCT means is provided with: a light-guiding means for guiding the signal-light; an image forming lens for focusing the signal-light emitted from said light-guiding means onto a position that is conjugate with the image forming surface of the image obtaining means; and a scanning means for moving the output face of the light-guiding means along a flat surface that is substantially parallel to the image focusing lens; and the image obtaining means, the light-guiding means, the image focusing lens, and the scanning means are provided within the endoscope insertion portion; and the scanning control means controls, by use of the scanning means, the positioning of the output face of the light emitting means; because the image focusing lens and the output face of the light-guiding means can be disposed above an axis substantially the same as that of the image obtaining lens, the diameter of the insertion portion of the endoscope apparatus is not increased, and the light guiding means, image focusing lens, and scanning means for obtaining an optical tomographic image can be provided within the insertion portion of the endoscope apparatus. Additionally, if the examination area is of a living-tissue subject and the wavelength of the low-coherence light is within the 600–1700 nm wavelength range, because the signal-light exhibits good transmittance and dispersion characteristics with respect to the living tissue, a desired optical tomographic image can be obtained.

In the case that the aforementioned examination area image obtaining means is an endoscope, as there is no need to insert a probe into the forceps port thereof to obtain an optical tomographic image, an optical tomographic image of the interior of a body cavity may be obtained without utilizing the forceps port of an endoscope. That is, as the forceps port becomes unnecessary in the obtaining of an examination area image and an optical tomographic image, the diameter of the endoscope can be made thin. In the case that a probe is utilized simultaneously to perform biopsies or other procedures, only one forceps port needs to be provided.

In addition, in the case that the aforementioned examination area image obtaining means is a surface examination probe, the provision of both a surface examination probe and an OCT detection element in the vicinity of the examination area becomes unnecessary, thereby obviating the need for a large space in the vicinity of the examination area.

BRIEF DESCRIPTION OF THE DRAWINGS

FIG. 1 is a schematic drawing of the first embodiment of the imaging apparatus according to the present invention.

FIG. 2 is a schematic drawing of the second embodiment of the imaging apparatus according to the present invention.

DESCRIPTION OF THE PREFERRED EMBODIMENTS

Hereinafter a description of the preferred embodiment of the present invention will be explained with reference to the attached drawing. FIG. 1 is a schematic drawing of the preferred embodiment of the imaging apparatus according to the present invention in its entirety. This imaging apparatus is one in which an OCT function is built into an endoscope, and comprises an insertion portion 10 to be inserted into a body cavity of a patient, an examination area image obtaining means 11 for obtaining an examination area image of an examination area 2 of the body of a patient, an OCT obtaining portion 12 for obtaining an optical tomographic image of a desired scanning area, and a display portion 13 for displaying an examination area image of the examination area 2 and an optical tomographic image of the scanning area.

The insertion portion 10 comprises: a forceps insertion port 101 extending internally therethrough to the distal end thereof; a CCD cable 102 extending internally therethrough to the distal end thereof; a light guide 103, and an optical fiber 156. A CCD photographing element 104 is connected to the distal end of the CCD cable 102. An illuminating lens 105 is provided at the distal end of the light guide 103, that is, at the distal end of the insertion portion 10. Further, an image obtaining lens 106 is provided at the distal end of the insertion portion 10, and a dichroic prism 107 is provided on the inner side of this image obtaining lens 106, that is, on the side of the image obtaining lens 106 opposite that facing toward the target subject. An image focusing lens 108 is provided on the still further inner side of the dichroic prism 107, and the output face 109 of the fiber 156 is disposed on the still further inner side of this image focusing lens 108. A Piezo actuator 110, which is a scanning means, is attached near the output face 109 of the fiber 156. Further, the Piezo actuator 110 is connected to a scanning position control portion 170, which is described below.

The light guide 103 is formed of a composite glass fiber, and is connected to the examination area image obtaining portion 11. The dichroic prism 107 separates the white-light L1 reflected from the examination area 2 and the signal-light L7' reflected from a predetermined depth of the scanning area. The dichroic prism 107 transmits light having a wavelength of 750 nm an higher, and perpendicularly reflects light having a wavelength shorter than 750 nm.

Further, the image forming lens 108 is disposed along the same axis as the image obtaining lens 106 and in the position for focusing the signal-light L7 emitted from the fiber 156 onto the position that is conjugate with the image forming surface of the CCD photographing element 104. Further, the image forming lens 108 is disposed parallel to the image obtaining lens 106, and the Piezo actuator 110 moves the output face 109 of the fiber 156 within a plane parallel to the image obtaining lens 106 and the image obtaining lens 108.

The examination area image obtaining means 11 comprises a white-light source 121 that emits a white-light L1 for obtaining an examination area image, a lens 122 that causes the white-light L1 emitted from said white-light source 121 to enter the light guide 103, and an image processing portion 123 for carrying out image processing on an examination area image obtained by the CCD photographing element 104 and outputting the examination area image signal formed thereby to the monitor 202, which is described below.

The image processing portion 123 subjects an image obtained by the CCD photographing element to signal processing to form an image signal, and after being digitized, said image signal is temporarily stored in a memory (not shown). The image signal is read out from the memory in synchronization with a display timing, and after being D/A converted, is further converted to a video signal and output to the monitor 202.

The OCT portion 12 comprises: a light source 140 for emitting a low-coherence light L5 having a core wavelength of 800 nm and a coherence length of 20 um; a fiber optics coupling system 150 for separating and combining the reference-light L6 and the signal-light L7 of the low-coherence light; an optical path extending portion 160 disposed along the optical path of the reference-light L6, which causes the length of the optical path of said reference-light L6 to change; a scanning control portion 170 for controlling the scanning with the signal-light L7 by the Piezo actuator disposed in the insertion portion 10; a balance differential detecting portion 180 for detecting the signal strength of the interference signal caused by the interference between the signal-light L7' reflected from a predetermined surface of the living tissue measurement area 1 and the reference-light L6; and a signal processing portion 190 for forming an image signal based on the signal strength of the interference signal detected by said balance differential detecting portion 180.

The light source 140 is provided with an SLD 141 for emitting a low-coherence light L5, and a lens 142 for focusing the low-coherence light L5 emitted from said SLD 141.

The fiber optics coupling system 150 comprises: a fiber coupler 151 for separating the low-coherence light emitted from the SLD 141 into a signal-light L7 and a reference-light L6, and for combining the signal-light L7' of the signal-light L7 reflected from a predetermined depth of the living tissue measurement area 1 and the reference-light L6 to obtain a combined-light L8; a fiber coupler 152 provided between the light source portion 140 and the fiber coupler 151; a Piezo element 153 for causing a slight shift in the frequency of the reference-light L6; a fiber 154 for connecting the light source portion 140 and the fiber coupler 152; a fiber 155 for connecting the balance differential detecting portion 180 and the optical path extending portion 160, by way of the fiber couplers 151 and 152; and a fiber 156 for connecting the insertion portion 10 and the balance differential detecting portion 180 by way of the fiber coupler 151. Note that the fibers 154, 155, and 156 are single mode optical fibers.

The optical path extension portion 160 comprises: a lens 161 for converting the reference-light L6 emitted from the fiber 155 to a parallel light and for causing the reflected reference-light L6 to enter the fiber 155; a prism 162 for changing the length of the optical path of the reference-light L6 by moving said prism in the horizontal direction indicated in FIG. 1.

The balance differential detecting portion 180 comprises a photodetector 181 and a photodetector 182 for detecting the interference signal due to the interference from the combined-light L8, and a differential amplifier 183 for adjusting the input balance of the detection values output by the photodetectors 151 and 152 and canceling out the noise component and drift component thereof, and then amplifying the difference therebetween.

The signal processing portion 190 performs a heterodyne detection process to obtain the intensity of the signal-light L7' reflected from a predetermined depth of the living tissue measurement area 1 from the signal strength of the interference signal detected by the balance differential detecting portion 180, converts the obtained intensity to an image signal, and outputs said image signal to the monitor 201.

The display portion 13 is provided with a monitor 201, which is an optical tomographic image display means for displaying an optical tomographic image, a monitor 202, which is an examination area image display means for displaying an examination area image, and an input portion 203, which is a pen-type position specifying means for specifying a desired pixel position on the examination area image. Note that each part is connected to a controller (not shown), which controls he operational timing thereof.

Next, the operation of the endoscope apparatus of the preferred embodiment of the present invention will be explained. First, the operator inserts the insertion portion 10 of the endoscope apparatus into a body cavity of the patient, and an examination area image is displayed on the monitor 202. At this time, first, the white-light L1 emitted from the white-light source 121 of the examination area image obtaining means 11 enters the light guide 103 by way of the lens 122, and after being guided to the distal end of the insertion portion 10, said white-light L1 is projected onto the interior of the body cavity by the illuminating lens 105.

The reflected-light L2 of the white-light L1 is focused by the image obtaining lens 106, reflected by the dichroic prism 107, and focused on the CCD photographing element 104. The obtained image signal, which has been photoelectrically converted by the CCD photographing element 104, is outputted to the image processing portion 123 via the CCD cable 102.

At the image processing portion 123, first, the image signal obtained by the CCD photographing element 104 is subjected to signal processing such as amplification, 2-bit relative sampling, clamping, blanking, etc., and an image signal is computed. Then, the image signal is digitized and stored in a memory. The image signal readout from the memory in synchronization with the display timing, after being D/A converted, is further converted to a video signal and output to the monitor 202.

While viewing an image of the interior of the body cavity 1 displayed on the monitor 202, the operator manually moves the insertion portion to a position in which the distal end thereof faces a desired examination area 2 including a living tissue measurement area 1, such as that shown in FIG. 1, and an image of the examination area 2 is displayed on the monitor 202. Then, the operator specifies the measurement starting position A and the measurement finishing position B of the operation to obtain an optical tomographic image, by use of the pen-type position specifying means 203, on the examination area image displayed on the monitor 202.

The scanning control portion 170 of the OCT obtaining portion 12 computes the scanning position on the examination area 2 to be scanned with the signal-light L7, based on the pixel positions of the measurement starting position A and the measurement finishing position B inputted at the monitor 202, and controls the Piezo actuator of the insertion portion 10 as well as the position of the output face 1009 of the fiber 156.

At this time, the signal-light L7 emitted from the output face 109 of the fiber 156 is focused by the image forming lens 108 onto the position that is conjugate with the image forming surface of the CCD photographing element 104. The output face 109 of the fiber 156 is moved within a plane that is parallel relative to the image forming lens 108 by the Piezo actuator 110, and because the point at which the signal-light L7 is projected moves, the focusing point also moves within the plane that is conjugate with the image forming surface of the CCD photographing element 104. Because this image forming point is again focused by the image obtaining lens 106, the image forming point on the examination area 2 is moved.

Therefore, if the measurement starting point A and the measurement starting point B are inputted on the examination area image displayed on the monitor 202, the pixel positions on the CCD photographing element 104 corresponding to the measurement starting point A and the measurement starting point B can be computed, and the position data of the conjugate point corresponding thereto can also be obtained. Based on this position data, the scanning control portion 170 controls the Piezo actuator 110, and the output face 109 of the fiber 156 is moved so that the image forming point of the signal-light L7 emitted from the output face 109 of the fiber 156 and focused by the image forming lens 108 moves in a manner that connects a straight line between the conjugate points of the measurement starting point A and the measurement starting point B.

Controlled in this way, the signal-light L7 scans the scanning area connecting the points corresponding to the position defined by the measurement starting point A and the measurement starting point B on the examination area 2, and an optical tomographic image of this scanning area is obtained by the OCT obtaining portion 12 and displayed on the monitor 201.

When an optical tomographic image is to be obtained, the low-coherence light L5 having a core wavelength of substantially 800 nm and a coherence length of 20 nm is emitted from the SLD 141, said low-coherence light L5 is focused by the lens 142 and enters the fiber 154.

The low-coherence light L5 conveyed by the fiber 154 enters the fiber 155 at the fiber coupler 152, and is separated into the reference-light L6, which proceeds within the fiber 155 in the direction of the optical path extending portion 160, and the signal-light L7, which proceeds within the fiber 156 in the direction of the scanning control portion 170, at the fiber coupler 151.

The reference-light L6 is modulated by the Piezo element 153 provided along the optical path, which causes a slight difference in frequency $\Delta f$ to occur between the reference-light L6 and the signal-light L7.

The signal-light L7 enters the insertion portion 10 by way of the fiber 156 and is emitted from the output face 109, focused by the image focusing lens 108, transmitted by the dichroic prism 107, again focused by the image obtaining lens 106, and projected onto the target subject 2. Note that at this time, the output face 109 of the fiber 156 is moved by the Piezo actuator 110 to the position indicated by the broken line shown in FIG. 1, and the signal-light L7 is projected onto the position of the examination area 2 corresponding to the measurement starting position A. The signal-light L7', which is the component of the signal-light L7 entering the examination area 2 that has been reflected at a predetermined depth thereof, is fed back to the fiber 156 by the image obtaining lens 106 and the image forming lens 108. The signal-light L7' fed back to the fiber 156 is combined within the fiber coupler 151 with the reference-light L6 fed back to the fiber 155, which is described below.

On the other hand, the reference-light L6 that has been modulated by the Piezo element 153 passes through the fiber 155 and enters the prism 162 through the lens 161 of the optical path extending portion 160, said modulated reference-light L6 is then reflected by the prism 162 and is again transmitted by the lens 161 and fed back to the fiber 155. The reference-light L6 fed back to the fiber 155 is combined in the fiber coupler 151 with the signal-light L7' described above.

The signal-light L7' and the reference-light L6 combined in the fiber coupler 151 are again combined along the same axis, and at a predetermined timing, interference is caused between said signal-light L7' and reference-light L6, whereby said signal-light L7' and reference-light L6 become a combined-light L8 and a beat signal (an interference signal) is produced.

Because the signal-light L7' and the reference-light L6 are low-coherence light of a short interference-susceptibility distance, after the low-coherence light has been separated into the signal-light L7 and the reference-light L6, if the length of the optical path of the signal-light L7 (L7') up to the point at which said signal-light L7 (L7') arrives at the fiber coupler 151 is substantially the same as the length of the optical path of the reference-light L6 up to the point at which said reference-light L6 arrives at the fiber 151, both of said lights interfere with each other, said interference repeats in a strong-weak cycle according to the difference Δf between the frequencies of the reference-light L6 and the signal-light L7, and a beat signal is generated thereby.

The combined-light L8 is separated in the fiber coupler 151: one of the separated components thereof enters the photodetector 181 of the balance differential detector 180 after passing through the fiber 155; and the other of the separated components thereof enters the photodetector 182 after passing through the fiber 156.

The photodetectors 181 and 182 detect the signal strength of the beat signal from the combined-light L8, and the differential amplifier 183 obtains the difference between the detection value of the photodetector 181 and the detection value of the photodetector 182 and outputs said difference to the signal processing portion 190. Note that because the differential amplifier 183 is provided with a function for adjusting the balance of the direct current component of the value input thereto, even in a case, for example, in which drift occurs in the low-coherence light emitted from the light source portion 140, by amplifying the difference after adjusting the balance of the direct current component, the drift component is cancelled out, and only the beat signal is detected.

Note that at this time, the prism 162 is aligned with the direction of the light axis (the horizontal direction appearing in FIG. 1). Therefore, because the length of the optical path of the reference-light L6 up to the point at which said reference-light L6 arrives at the fiber coupler 151 changes, and the length of the optical path of the signal-light L7 (L7') changes, the depth at which the tomographic data of the living tissue measurement area 1 is obtained changes.

According to the operation described above, after the tomographic data of a desired depth from the point on the surface of a target subject 2 corresponding to the measurement starting point A has been obtained, the output face 109 of the fiber 156 is moved by the Piezo actuator 110, under the control of the scanning control portion 170, toward the lower direction shown within FIG. 1. According to this operation, the entry point of the signal-light L7 is also moved slightly in the direction of the measurement finishing point B, and the tomographic data is obtained to a predetermined depth in the same way. By repeating the above-described operation, the optical tomographic data of the scanning area corresponding to the measurement starting point A and the measurement starting point B of the target subject 2 can be obtained.

The signal processing portion 190 performs a heterodyne detection to detect the strength of the signal-light L7' reflected by a predetermined surface of the target subject 2 from the signal strength of the signal-light Ls, converts the obtained strength of the signal-light Ls' to optical tomographic data, and outputs said optical tomographic data to the monitor 13 and the diagnostic data output portion 180 of the data output portion 12.

According to the above described configuration and operation, the imaging apparatus of the present invention can obtain an optical tomographic image of the interior of a body cavity of a patient without requiring the insertion of a probe for obtaining an optical tomographic image through the forceps insertion port 101, that is to say, without using the forceps insertion port 101 of the endoscope apparatus. Therefore, even if only one forceps insertion port is provided, the obtaining of an optical tomographic image and other procedures such as biopsies utilizing a probe to be inserted into forceps insertion port 101 can be performed concurrently, and the overall convenience attained in the practical application of the imaging apparatus is improved. Note that for cases in which it is not necessary to provide the imaging apparatus with a forceps insertion port, an imaging apparatus provided with an OCT function can be miniaturized.

Further, because the examination area image is displayed on the monitor 202 and the optical tomographic image is displayed concurrently on the monitor 201, an operator can observe both the examination area image and the optical tomographic image concurrently, whereby the overall convenience attained in the practical application of the endoscope apparatus is improved.

In addition, by arbitrarily specifying 2 desired points on an examination area image displayed on the examination area image display means by use of the pen-type input portion 203, because an optical tomographic image of the scanning area corresponding to the target subject between said 2 specified desired points is obtained, it becomes unnecessary to perform a troublesome manual operation for causing the signal-light L7 to be guided to a desired position, and an optical tomographic image of a desired position can be accurately obtained.

Because the fiber 156 for guiding the signal-light L7, the focusing lens 108 for focusing the signal-light L7 emitted from the fiber 156, and the Piezo actuator 110 for moving the position of the output face 109 of the fiber 156 can be disposed along substantially the same axis as the image obtaining lens 106, the width of the diameter of the insertion portion 10 of the endoscope apparatus is not increased, and an optical system for obtaining an optical tomographic system can be built into the insertion portion 10.

Additionally, because the wavelength of the low-coherence light is 800 nm, the signal-light exhibits good transmittance and dispersion characteristics with respect to the examination area 2, and a desired optical tomographic image can be obtained.

Note that as an example of an alternative embodiment of the present invention: three or more specifying points can be specified by use of the input portion 203; the area enclosed within said specified specifying points can be the scanning area; an optical tomographic image of this scanning area can be obtained; and a 3-dimensional optical tomographic is obtained; in this case, by a simple operation, a 3-dimensional optical tomographic can also be obtained, and the overall convenience attained in the practical application of the endoscope apparatus is improved a level.

Next, the second embodiment of the present invention will be described with reference to FIG. 2. FIG. 2 is a schematic view of the imaging apparatus of the present invention. Note that elements that are the same as those described in the first embodiment of FIG. 1 are labeled with the same reference numerals, and insofar as further explanations thereof are unnecessary, they have been omitted.

This imaging apparatus is one in which an OCT function is built in to a surface examination probe, and comprises: a surface examination probe 20 to be held by a user; an examination area image obtaining means for obtaining an examination area image of examination area 2' of a living subject; an OCT obtaining portion 12 for obtaining an optical tomographic image of a desired scanning area; and a display portion 13 for displaying an examination area image of examination area 2' and an optical tomographic image of a scanning area.

The surface examination probe 20 comprises: a pen-shaped grip cover 211; a CCD cable 102 in the interior of said grip cover 211 that extends to the distal end thereof; a light guide 103; and an optical fiber 156. A CCD imaging element is connected to the distal end of CCD cable 102. An illuminating lens 105 is provided the distal end of light guide 103, that is, in the vicinity of the distal end of the surface examination probe 20. In addition, an image obtaining lens 106 is provided in the vicinity of the distal end of the surface examination probe 20. A dichroic prism 107 is provided within the grip cover 211, in a position further inward in relation to the image obtaining lens 106. An image forming lens 108 is provided still further inward in relation to the dichroic prism 107, and the emission end 109 of optical fiber 156 is positioned inward of the image forming lens 108. A piezo actuator 100 that acts as the scanning means is mounted in the vicinity of the emission end 109 of the optical fiber 156. Further, the piezo actuator 100 is connected to scanning position control portion 170.

The user holds the surface examination probe 20 of the imaging apparatus in the vicinity of the examination area 2' of a subject and displays the examination area image on monitor 202. If a measurement start point A and measurement end point B is input on the examination area image displayed on monitor 202 as in the first embodiment, the signal light 17 will scan the area between the points of examination area 2' corresponding to measurement start point A and measurement point B. The OCT obtaining portion 12 obtains an optical tomographic image of this scan area, that is, of the living subject measurement area 1', and displays said image on monitor 201.

As has been made clear by the description above, the present embodiment, in addition to the effects provided by the first embodiment, obviates the need for a large space in the vicinity of an examination area for the placement of a surface examination probe and an OCT detection element.

What is claimed is:

1. An imaging apparatus comprising:
an examination area image obtaining means having an illuminating light emitting means for projecting an illuminating light onto a target subject, an image obtaining means for obtaining an image formed of the reflected light which is reflected from the target subject upon the irradiation thereof with the illuminating light emitted from said illuminating light emitting means and which has passed through an image obtaining lens, an examination area image display means for displaying an examination area image based on said image obtained by said image obtaining means,
and an optical coherence tomography (OCT) means for scanning a predetermined scanning area within the target subject with a signal light, which is a low coherence light, and obtaining an optical tomographic image of the scanned area using the interference caused between the reflected light reflected from a predetermined depth of said scanning area upon the scanning thereof with the signal light, and a reference-light which has a slight frequency difference with respect to the signal light, wherein the OCT means performs the scanning of the examination area by passing the signal light through the image obtaining lens.

2. An imaging apparatus as defined in claim 1, further comprising
an optical tomographic image display means for displaying an optical tomographic image obtained by the OCT means, wherein
said optical tomographic image display means can also be a means for concurrently displaying the examination area image and the optical tomographic image.

3. An imaging apparatus as defined in claim 1, further comprising
a position specifying means for arbitrarily specifying two desired points on an examination area image displayed on the examination area image display means, wherein
the OCT means may further comprise a scanning control portion for scanning with the signal light the scanning area corresponding to the position between the two points specified by use of the position specifying means.

4. An imaging apparatus as defined in claim 2, further comprising
a position specifying means for arbitrarily specifying two desired points on an examination area image displayed on the examination area image display means, wherein
the OCT means may further comprise a scanning control portion for scanning with the signal light the scanning area corresponding to the position between the two points specified by use of the position specifying means.

5. An imaging apparatus as defined in claim 3, wherein said OCT means comprises,
a light guiding means for guiding the signal light,
an image forming lens for focusing the signal light emitted from said light guiding means onto the position that is conjugate with the image forming surface of the image obtaining means, and
a scanning means for moving the output face of the light guiding means along a plane that is substantially parallel to the image focusing lens, wherein
the image obtaining means, the light guiding means, the image focusing lens, and the scanning means are provided within the endoscope insertion portion, and the scanning control means controls, by use of the scanning means, the positioning of the output face of the light guiding means.

6. An imaging apparatus as defined in claim 4, wherein said OCT means comprises,
a light guiding means for guiding the signal light, an image forming lens for focusing the signal light emitted from said light guiding means onto the position that is conjugate with the image forming surface of the image obtaining means, and a scanning means for moving the output face of the light guiding means along a plane that is substantially parallel to the image focusing lens, wherein
the image obtaining means, the light guiding means, the image focusing lens, and the scanning means are provided within the endoscope insertion portion, and
the scanning control means controls, by use of the scanning means, the positioning of the output face of the light guiding means.

7. An imaging apparatus as defined in any one of claims 1, 2, 3, 4, 5, or 6 wherein said examination area is of a living tissue subject, and the wavelength of the low-coherence light is within the 600–1700 nm wavelength range.

8. An imaging apparatus as defined in any one of claims 1, 2, 3, 4, 5, or 6 wherein
said examination area image obtaining means is an endoscope.

9. An imaging apparatus as defined in any one of claims 1, 2, 3, 4, 5, or 6 wherein
said examination area image obtaining means is a surface examination probe.

10. An imaging apparatus as defined in claim 7 wherein said examination area image obtaining means is an endoscope.

11. An imaging apparatus as defined in claim 7 wherein said examination area image obtaining means is a surface examination probe.

* * * * *